United States Patent [19]

Reever et al.

[11] Patent Number: 4,778,786
[45] Date of Patent: Oct. 18, 1988

[54] COMPOSITION FOR TRANSDERMAL DRUG DELIVERY

[75] Inventors: Richard Reever, Plato; Larry Lundmark, Brooklyn Park; Timothy Kapsner, Minneapolis, all of Minn.

[73] Assignee: Minnetonka, Inc., Minnetonka, Minn.

[21] Appl. No.: 119,156

[22] Filed: Nov. 10, 1987

Related U.S. Application Data

[63] Continuation-in-part of Ser. No. 719,335, Apr. 3, 1985, abandoned.

[51] Int. Cl.⁴ .................. A61K 9/70; A61K 31/60; A61K 31/62
[52] U.S. Cl. .................. 514/54; 106/205; 106/207; 106/208; 424/449; 514/61; 514/159; 514/164; 514/944; 514/947; 514/965
[58] Field of Search .......... 424/449; 514/54, 61, 514/159, 164, 944, 947, 965; 106/205, 207, 208

[56] References Cited

U.S. PATENT DOCUMENTS

| | | |
|---|---|---|
| Re. 31,454 | 12/1983 | Hymes .................. 128/641 |
| 3,343,540 | 9/1967 | Siegel .................. 514/164 |
| 3,475,363 | 10/1969 | Gander .................. 523/111 |
| 3,612,053 | 10/1971 | Pratt .................. 604/338 |
| 3,640,741 | 2/1972 | Etes .................. 106/170 |
| 3,972,995 | 8/1976 | Tsuk et al. .................. 424/28 |
| 4,226,848 | 10/1980 | Nagai et al. .................. 514/313 |
| 4,250,163 | 2/1981 | Nagai et al. .................. 106/35 |
| 4,253,460 | 3/1981 | Chen et al. .................. 604/336 |
| 4,274,420 | 6/1981 | Hymes .................. 128/641 |
| 4,299,231 | 11/1981 | Karmann et al. .................. 106/208 |
| 4,306,551 | 12/1981 | Hymes et al. .................. 128/156 |
| 4,307,717 | 12/1981 | Hymes et al. .................. 128/156 |
| 4,359,483 | 11/1982 | Kaetsu et al. .................. 427/2 |
| 4,514,385 | 4/1985 | Damani et al. .................. 514/164 |
| 4,675,009 | 6/1987 | Hymes et al. .................. 424/448 |

FOREIGN PATENT DOCUMENTS

| | | |
|---|---|---|
| 2913296 | 10/1979 | Fed. Rep. of Germany ...... 514/164 |
| 58-144315 | 8/1983 | Japan .................. 514/164 |
| 151174 | 9/1920 | United Kingdom .................. 514/159 |
| 650381 | 2/1951 | United Kingdom .................. 514/164 |

OTHER PUBLICATIONS

The Merck Index, Tenth Edition, published by Merck & Co., Inc., Rahway, N.J., U.S.A., 1983, p. 1200 (Item 8190).

Primary Examiner—Ronald W. Griffin
Attorney, Agent, or Firm—Dorsey & Whitney

[57] ABSTRACT

As a composition for transdermal drug delivery, the gelation reaction product of a mixture of an organic polysaccharide gum, polyethylene glycol, and m-, p- or o-hydroxybenzoic acid in an amount effective in forming from such mixture a gel having adhesive properties for adhesion to skin and being sufficiently pliant to conform to the shape of body contours.

18 Claims, 1 Drawing Sheet

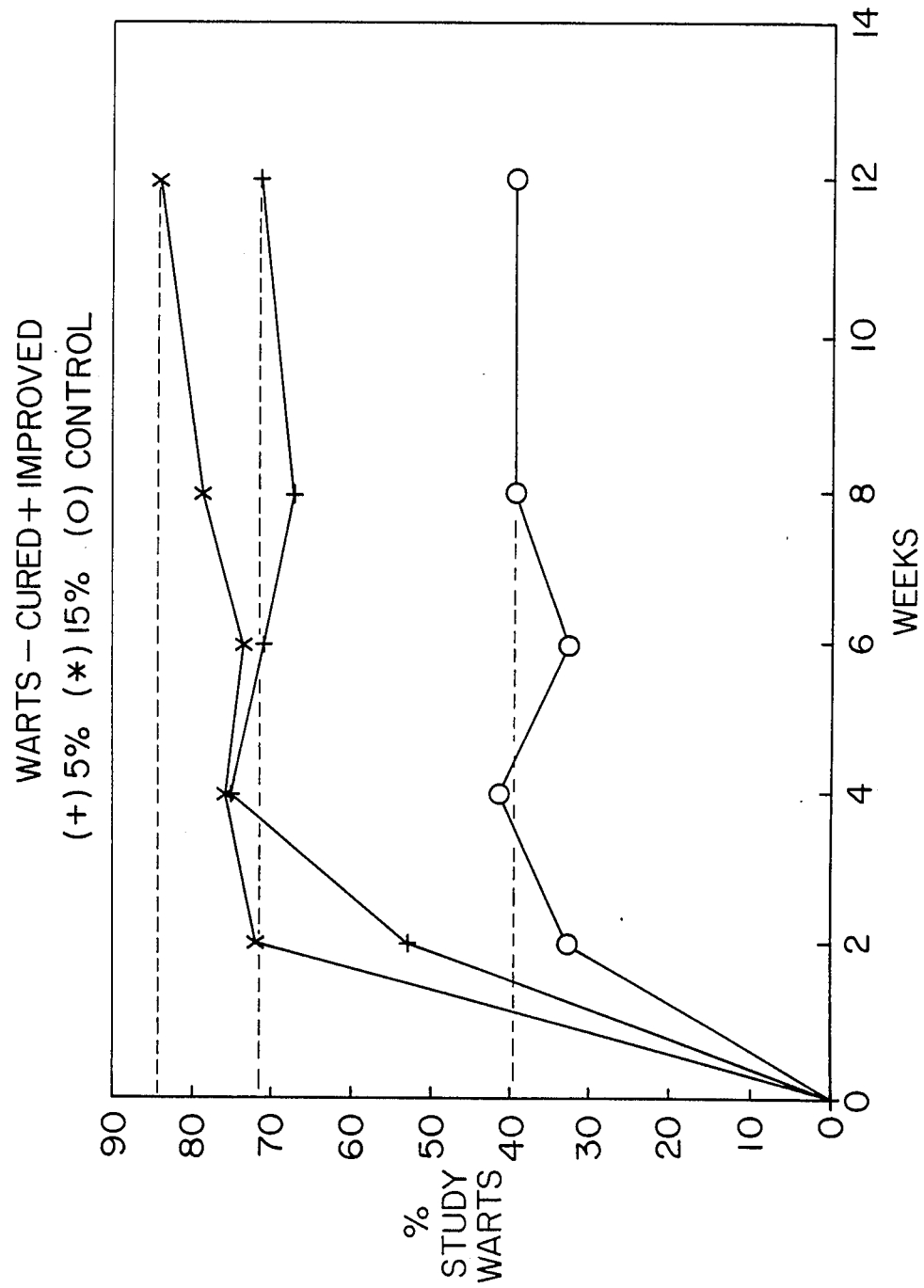

COMPOSITION FOR TRANSDERMAL DRUG DELIVERY

This application is a file wrapper continuation-in-part of application Ser. No. 719,335, filed Apr. 13, 1985, now abandoned.

BACKGROUND OF THE INVENTION

1. Field of the Invention

This invention relates to a transdermal drug delivery vehicle which is particularly useful for topical application to a person's skin of salicylic acid and other drugs such as hydroquinone.

2. Description of the Prior Art

Sterculia gum, also known as gum karaya, is a hydrophilic colloid made from exudate of the Sterculia Urens tree. It is a complex polysaccharide gum with a molecular weight of almost 10 million. It contains approximately 8% acetyl groups and 37% uronic acid residues, being comprised mainly of D-galacturonic acid, D-galactose and 1-rhamnose.

Sterculia gum has many known applications in the medical field. It has been used as a treatment for chronic skin ulcers, as a denture adhesive and as a bulk laxative. It has also been used as a skin adhesive with principal application as an adhesive ring for attaching stoma bags to patients.

Sterculia gum has been used in combination with hydric alcohols as an electrode for medical monitoring and stimulation through a person's skin. The mixture of the natural organic polysaccharide and hydric alcohol forms an adhesive capable of conducting electricity.

Sterculia gum has been used in combination with cross-linking agents such as propylene glycol plus a non-reactive water soluble carrier such as glycerol. Medication or cosmetic additives are dissolved in the carrier. U.S. Pat. No. 3,640,741, issued to Etes on Feb. 8, 1972, teaches that the mixture of gum and cross-linking agent forms a gel which traps the carrier and dissolved additive in the gel. The gel will dissolve slowly in a liquid medium such as mammalian body fluid, thereby providing for slow timed release of medication additives in the body or cosmetic additives on the surface of a person's skin.

Sterculia gum has been used in combination with a synthetic resin such as polyacrylic acid or polyacrylamide plus a carrier such as propylene glycol or glycerol. U.S. Pat. No. 4,307,717, issued to Hymes et al. on Dec. 29, 1981, teaches that the synthetic resin preserves dimensional stability of the delivery patch, even though the patch is irradiated to prevent unwanted growth of bacteria or fungus in and on the patch. The synthetic resin also preserves the dimensional stability of the delivery patch when the patch is in contact with body fluids appearing on the surface of the skin. The carrier embodied in the patch will deliver solubilized medicaments to the surface of the skin as the patch slowly adsorbs body fluids from the skin surface. The Hymes patent teaches that the medicament may be a keratolytic agent such as salicylic acid, but requires the presence of the synthetic resin to protect the patch during irradiation. The Hymes patent does not teach the use of polyethylene glycol.

Salicylic acid has been used for many years to treat common warts. The most common commercial form is a flexible collodion (e.g. Compound W, available from White Hall Laboratories, Division of American Home Products Corporation, New York City, N.Y. 10017). The salicylic acid is dissolved in a vehicle consisting of nitrocellulose and solvents such as alcohol and ether. The flexible collodion is applied to a wart where it dries to a white crust. The principal disadvantages include the messiness of the application procedure and the precipitation of the salicylic acid upon evaporation of the solvents.

A less common method of applying salicylic acid to the skin involves suspending salicylic acid at about 40% by weight concentration in an adhesive base which is adhered to a paper or cloth backing. This material is cut to size and held against the skin by waterproof tape.

Salicylic acid may also be used in treating hyperkeratotic conditions such as corns and calluses. The salicylic acid softens and destroys the stratum corneum by increasing endogenous hydration which causes the cornified epithelium to swell, soften, macerate and finally desquamate.

SUMMARY OF THE INVENTION

In accordance with the invention, it has been discovered that a gel, having adhesive properties for adhesion to the skin and being sufficiently pliant to conform to the shape of body contours, can be formed from a mixture of organic polysaccharide and polyethylene glycol provided that the mixture contain meta-, para- or ortho-hydroxybenzoic acid (i.e. m-, p- or o-hydroxybenzoic acid).

Based on the following examples, it is surmised that gels formed from mixtures of organic polysaccharides and drug carriers, in the absence of synthetic resins disclosed in the Hymes patent which alter structural integrity, vary in physical characteristics according to the concentration of the carrier. The physical characteristics vary between mushy gels corresponding to high concentrations of carrier and stiff or brittle gels corresponding to low concentrations of carrier. Toward the mushy end of the continuum, a gel is increasingly deformable and tacky (i.e. adhesive). Both deformability and tackiness are desirable in successfully adhering a gel patch to skin. Toward the stiff end of the continuum, a gel is increasingly resilient. This structural integrity is desirable for the handling of the gel patch during its manufacture. Structural integrity is also desirable because when a gel patch is adhering to the skin it adsorbs moisture, thereby degrading the gel patch in the direction of mushiness.

The present invention thus rests on the discovery that polyethylene glycol and m-, p- or o-hydroxybenzoic acid combine with polysaccharide gums to form a gel having both desirable tackiness/deformability and desirable structural integrity. In contrast, polyethylene glycol and polysaccharide gums, without m-, p- or o-hydroxybenzoic acid, mostly fail to form gels or form mushy gels lacking structural integrity even at modest concentrations of polyethylene glycol.

The composition for transdermal drug delivery of the present invention is a gelation reaction product of a mixture comprising an organic polysaccharide gum, polyethylene glycol and m-, p- or o-hydroxybenzoic acid. This mixture is effective in forming a gel having adhesive properties for adhesion to the skin and being sufficiently pliant to conform to the shape of body contours. The organic polysaccharide gum may be Sterculia gum. The hydroxybenzoic acid may be m-hydroxybenzoic acid, p-hydroxybenzoic acid or o-hydroxybenzoic acid (i.e. salicylic acid).

The foregoing gel may be used to deliver solubilized salicylic acid itself to the skin. It may also be used to deliver to the skin a non-hydroxybenzoic acid drug (i.e. a medicament or cosmetic) including hydroquinone.

BRIEF DESCRIPTION OF DRAWINGS

FIG. 1 shows the results of 5% and 15% salicylic acid delivery vehicles used in treatment of warts.

DESCRIPTION OF THE PREFERRED AND ALTERNATIVE EMBODIMENTS

In the preferred embodiment, about 5% to 15% powdered salicylic acid, about 45% to 35% powdered Sterculia gum (salicylic acid and Sterculia gum adding up to about 50%), about 25% polyethylene glycol, about 25% propylene glycol and about 0.2% quaternium-15 (available as Dowicil-200 from Dow Chemical, Midland, Mich.) are placed into a container and mixed at room temperature until a substantially homogeneous slurry is formed. All concentrations or amounts stated herein by percentage are percentage by weight of the mixture prior to the gelation reaction. The homogeneous slurry in the container is warmed slightly on a hot plate and stirred until the slurry begins to thicken slightly. The heating process assists in dissolving the various components and in initiating the gelation reaction.

The slightly thickened mixture is poured onto polymer-coated release paper. Another piece of release paper is placed on top of the mixture and flattened to desired thickness. The sandwich consisting of release paper and mixture may be heated in a convection or radiation oven at 100° C. and allowed to gel for 5 minutes. After cooling, the gelation reaction product may be cut to a preferred size of less than 3 mm thickness and less than 25 mm in diameter for treatment of warts.

In alternative embodiments, the amount of salicylic acid may vary within the range of about 3 to 25 percent of the weight of the mixture. The amount of Sterculia gum may vary within the range of about 15 to 55 percent of the weight of the mixture.

The polyethylene glycol may be a polymer of ethylene oxide that conforms generally to the formula $H(OCH_2CH_2)_nOH$ where n has some average value in the range of about 4 to 12. For example, the polyethylene glycol may be PEG-4, PEG-6, PEG-8, PEG-10 or PEG-12 (Cosmetic Toiletry and Fragrance Association designations where PEG-n designates $H(OCH_2CH_2)_nOH$) The preferred embodiment PEG-4 and PEG-6 are available commercially as Carbowax 200 and Carbowax 300 respectively from Union Carbide, Chicago, Ill.

In the preferred embodiment, polythylene glycol and propylene glycol are used. Alternatively, polyethylene glycol and glycerin or polyethylene glycol by itself or in combination with other hydroxybenzoic solvents or materials may be used.

The preferred preservative is about 0.2% quaternium-15 by weight of the mixture, but may also be paraben or other preservatives in small amounts generally less than 1% of the weight of the mixture.

EXAMPLE 1

Salicylic acid was varied according to the following: 0, 1, 2, 3, 5, 15, 25 and 35% by weight of the mixture. Steculia gum was held constant at 35%, while PEG-6 (Carbowax 300) and propylene glycol made up the remaining portion of the mixture in a 1:1 weight ratio. Without salicylic acid (i.e. at 0%), no gel formed upon heating the mixture. At 1% and 2% salicylic acid, a gel formed but the gel was deficient in structural integrity and disassociated. At 3, 5, 15 and 25% salicylic acid, a gel formed having desirable tacky and pliant characteristics as well as structural integrity. At 35% salicylic acid, an extremely tough and stiff gel formed and after 30 minutes at room temperature, the salicylic acid precipitated throughout the gel.

EXAMPLE 2

Salicylic acid was held constant at 15% and Sterculia gum was held constant at 35% by weight of the mixture. Preservative quaternium-15 was held constant at 0.2%. The remaining portion consisted of PEG-300 and propylene glycol in 1:1, 9:1 and 2:8 ratios by weight. The example was repeated substituting PEG-4 (Carbowax 200) for PEG-6.

The 1:1 ratio of PEG-4 or PEG-6 resulted in the most desirable combination of tackiness/pliancy and structural integrity. The 9:1 ratio resulted in a patch having increased structural integrity but decreased tackiness/pliancy. The 2:8 ratio resulted in a patch having increased tackiness/pliancy but decreased structural integrity. In all three cases, however, the mixture formed a usable transdermal drug delivery vehicle upon gelation.

EXAMPLE 3

Salicylic acid was held constant at 15% by weight of the mixture. Preservative quaternium-15 was held constant at 0.2%. Sterculia gum was varied according to the following: 10, 15 and 50% while PEG-6 and propylene glycol at 1:1 weight ratio made up the remaining portion of the mixture. Salicylic acid was lowered to 5%, Sterculia gum varied at 55 and 60%, with preservative and PEG-6/propylene glycol ratio as above.

At 10% Sterculia gum, a gel barely formed upon heating, but was deficient in structural integrity and easily disassociated. At 15 and 50% Sterculia gum, a gel formed having desirable tacky/pliant characteristics as well as structural integrity. At 55% Sterculia gum, a gel formed which was tough but deficient in tackiness/pliant characteristics. At 60% Sterculia gum, a gel did not form, with significant amounts of the powdered salicylic acid and powdered Sterculia gum remaining undissolved by the liquid.

EXAMPLE 4

In absence of salicylic acid, a gel did not form with more than 25% by weight of mixture of PEG-4, even if propylene glycol or glycerine in 1:1 ratio to PEG-4 were also included.

EXAMPLE 5

Salicylic acid at 15% and Sterculia gum at 35% by weight of the mixture were held constant. 50% propylene glycol was compared to 25% propylene glycol and 25% PEG-300. At 50% propylene glycol, a gel formed but which was softer and not as strong as the gel resulting from 25% propylene glycol and 25% PEG-6.

EXAMPLE 6

The mixture consisted of 15% meta-hydroxybenzoic acid, 24.9% PEG-6, 24.9% propylene glycol, 35% Sterculia gum and 0.2% quaternium-15. Alternatively, para-hydroxybenzoic acid was substituted for meta-hydroxybenzoic acid, the amounts of each component adjusted to yield the same percentages by weight. The resulting gelation reactions for each of the meta- and para-hydroxybenzoic acid mixtures required slightly additional heating than that for ortho-hydroxybenzoic acid (i.e. salicylic acid). As the hydroxyl group moves further away from the carboxylic acid group, the gel increases in structural integrity but decreases in tackiness/pliancy.

EXAMPLE 7

Hydroquinone at 1%, PEG-300 at 24.4%, propylene glycol at 24.4%, Sterculia gum at 55%, m-hydroxybenzoic acid at 15% and quaternium-15 at 0.2% by weight of mixture resulted in a gel with good tackiness/pliancy and structural integrity. Thus, the use of m-, p- or o-hydroxybenzoic acid, especially meta- and para- which do not redily react with skin, might be useful as part of a delivery vehicle for non-hydroxybenzoic drugs such as hydroquinone.

EXAMPLE 8

A clinical evaluation was conducted comparing 5% salicylic acid and 15% salicylic acid to a placebo control according to the following formulations:

| 5%/15% Salicylic Acid | Control |
| --- | --- |
| 5%/15% Salicylic Acid | 35% Sterculia Gum |
| 45%/35% Sterculia Gum | 57.5% Propylene Glycol |
| 24.9%/24.9% PEG-6 | 7.5% Water |
| 24.9%/24.9% Propylene Glycol | |
| 0.2%/0.2% Quaternium-15 | |

The placebo control involved a variant formulation in order to produce a gelled patch in the absence of salicylic acid.

The clinical research was conducted at two sites in the United States. The investigators for both studies were practicing professionals active in dermatology and the treatment of warts. 119 people completed the study with a total of 377 warts. The study lasted 12 weeks and included regular visits to the investigator for evaluation. Effectiveness of the drug was measured in terms of significant reduction in the size of the wart or in its complete removal versus no change in size. Total effectiveness of the treatment was compared with the placebo. From prior wart removal clinical studies and discussion in the literature, a treatment is termed effective if the difference between treatment and control cured and improved rate is greater than 20% for the approximate test population size used here.

Below are general effectiveness ratings for common warts (V.V. warts) for both 5 and 15% salicylic acid treatments and placebo at 12 weeks:

| Treatment | % Cured and Improved |
| --- | --- |
| 5% Salicylic Acid | 72 |
| 15% Salicylic Acid | 85 |
| Placebo Control | 40 |

The differential in cure between treatment and control is significantly greater than 20% at 12 weeks. FIG. 1 shows the results throughout the 12 week period.

EXAMPLE 9

A formulation was prepared having the following composition:

| PEG-6 | 25.0 |
| --- | --- |
| Propylene Glycol | 24.8 |
| Salicylic Acid | 15.0 |
| Karaya | 35.0 |
| Quaternium-15 | 0.2 |

"Average tack" for this formulation was measured using a Chatillon Universal Test Stand, Model UTSE, commercially available from John Chatillon and Sons, New York, N.Y., with the variable speed rheostat set at 2. The Chatillon instrument measures the force required to separate the tested material from one of two metal plates to which the test material is adhered. Eight tests of the above-described formulation yielded an average tack value of 1.23 pounds.

EXAMPLE 10

A formulation was prepared containing 2-acrylamido-2-methylpropanesulfonic acid ["AMPS"] in a polymerized form. AMPS is commercially available from Lubrizol Corporation, Wickliffe, Ohio, and has the following composition:

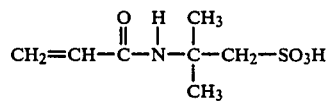

Additional information relating to AMPS may be found in Jevne, et al., U.S. Pat. No. 4,650,614, the disclosure of which is incorporated by reference as if fully set forth herein. The polymerized form of AMPS is commercially avaiable from Henkel Corp., 1301 Jefferson Street, Hoboken, N.J., as "HSP-1180" and has the following formula:

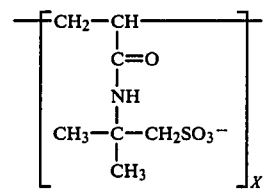

wherein X has a value such that the molecular weight of the anionic portion of the polymer is from about 1,000,000 to about 5,000,000. Additional information relating to the polymer of AMPS and its production may be found in Lundmark, et al., U.S. Pat. No. 4,128,631, the disclosure of which is incorporated by reference as if fully set forth herein.

Two formulations were prepared having the following compostions:

| | Formulation 1 | Formulation 2 |
| --- | --- | --- |
| HSP-1180 | 1.0% | — |
| PEG-6 | 10.0 | 10.0% |
| Propylene Glycol | 44.8 | 44.8 |
| Salicylic Acid | 15.0 | 15.0 |
| Karaya | 29.0 | 30.0 |

| | Formulation 1 | Formulation 2 |
|---|---|---|
| Quaternium-15 | 0.2 | 0.2 |

Both formulations were tested for average tack using the Chatillon instrument described in Example 9. The formula containing 1.0% AMPS polymer had an average tack value of 1.37 pounds. The formula containing no AMPS polymer had an average tack value of 0.60 pounds. The Student's T-Distribution Test indicated that these values were significantly different at 99.99% confidence. The increase in average tack with addition of the AMPS polymer is reflected in a corresponding significant increase in adhesion of the material to skin. The addition of AMPS polymer produces no evidence indicating a change in any other physical properties of patches made using the AMPS polymer formulation. As a result, transport properties of such patches are not expected to change upon of addition of the AMPS polymer.

From the foregoing, it will be obvious to those skilled in the art that various modifications in the above described methods and materials can be made without departing from the spirit of the invention. Accordingly, the invention may be embodied in other specific forms without departing from the spirit of the invention. Present embodiments are to be considered in all respects as illustrative and not restrictive, the scope of the invention being indicated by the appended claims rather than by the foregoing descriptions, and changes which come within the meaning and range of equivalency of the claims are therefore intended to be embraced therein.

We claim:

1. As a composition for transdermal drug delivery, the gelation reaction product of a mixture comprising:
   an organic polysaccharide gum;
   polyethylene glycol; and
   m-, p- or o-hydroxybenzoic acid.

2. The gelation reaction product of claim 1 wherein the organic polysaccharide gum is Sterculia gum.

3. The gelation reaction product of claim 1 wherein the m-, p- or o-hydroxybenzoic acid is o-hydroxybenzoic acid and such o-hydroxybenzoic acid is substantially solubilized in the reaction product for delivery to skin.

4. The gelation reaction product of claim 1 wherein the mixture further comprises a solubilized non-hydroxybenzoic acid drug.

5. The gelation reaction product of claim 4 wherein the solubilized non-hydroxybenzoic acid is hydroquinone.

6. The gelation reaction product of claim 1 wherein the amount of the m-, p- or o- hydroxybenzoic acid contained in the mixture is effective in forming from such a mixture a gel having structural integrity, being adhesive to skin and being pliant to conform to the shape of body contours.

7. The gelation reaction product of claim 6 wherein the organic polysaccharide gum is Sterculia gum and the m-, p- or o-hydroxybenzoic acid is o-hydroxybenzoic and the effective amount of the o-hydroxybenzoic acid is in the range of about 3 to 25 percent of the weight of the mixture.

8. The gelation reaction product of claim 7 wherein the amount of Sterculia gum is in the range of about 15 to 55 percent of the weight of the mixture.

9. The gelation reaction product of claim 1 wherein the mixture further comprises propylene glycol.

10. The gelation reaction product of claim 1 wherein the mixture further comprises glycerin.

11. The gelation reaction product of claim 1 wherein the polyethylene glycol is a polymer of ethylene oxide that conforms generally to the formula $H(OCH_2CH_2)_nOH$ where n has some average value in the range of about 4 to 12.

12. The gelation reaction product of claim 11 wherein n has some average value in the range of about 4 to 6.

13. The gelation reaction product of claim 12 wherein the polyethylene glycol has the formula $H(OCH_2CH_2)_4OH$ or $H(OCH_2CH_2)_6OH$.

14. The gelation reaction product of claim 1 wherein the mixture further comprises a perservative.

15. The gelation reaction product of claim 1 wherein the gelation reaction product is in the form of a mass less than 3 mm thick and less than 25 mm in diameter.

16. The gelation reaction product of claim 1 wherein the reaction product is a sheet less than 3 mm thick.

17. The gelation reaction product of claim 1 wherein the mixture further comprises a polymer of 2-acrylamido-2-methylpropanesulfonic acid.

18. The gelation reaction product of claim 17 wherein the molecular weight of the anionic portion of the polymer of 2-acrylamido-2-methylpropanesulfonic acid is from about 1,000,000 to 5,000,000.

* * * * *

UNITED STATES PATENT AND TRADEMARK OFFICE
CERTIFICATE OF CORRECTION

PATENT NO. : 4,778,786

DATED : October 18, 1988

INVENTOR(S) : Richard Reever, Larry Lundmark and Timothy Kapsner

It is certified that error appears in the above-identified patent and that said Letters Patent is hereby corrected as shown below:

In Column 5, line 12, delete "55%" and insert --35%--.

In Column 8, line 16, before "and", insert --acid--.

In Column 8, line 37, delete "perservative" and insert --preservative--.

Signed and Sealed this

Twenty-seventh Day of June, 1989

Attest:

DONALD J. QUIGG

*Attesting Officer*  *Commissioner of Patents and Trademarks*